United States Patent
Wöhrle et al.

(10) Patent No.: US 7,674,765 B2
(45) Date of Patent: Mar. 9, 2010

(54) METHOD FOR PRODUCING CYCLOHEXADECANONE

(75) Inventors: Ingo Wöhrle, Holzminden (DE); Walter Kuhn, Holzminden (DE); Hans-Ulrich Funk, Lauenforde (DE); Alfred Körber, Holzminden (DE)

(73) Assignee: Symrise GmbH & Co., KG, Holzminden (DE)

( * ) Notice: Subject to any disclaimer, the term of this patent is extended or adjusted under 35 U.S.C. 154(b) by 1500 days.

(21) Appl. No.: 10/516,006

(22) PCT Filed: May 22, 2003

(86) PCT No.: PCT/EP03/05342

§ 371 (c)(1),
(2), (4) Date: Nov. 29, 2004

(87) PCT Pub. No.: WO03/099753

PCT Pub. Date: Dec. 4, 2003

(65) Prior Publication Data

US 2006/0089296 A1    Apr. 27, 2006

(30) Foreign Application Priority Data

May 29, 2002  (DE) .............................. 102 23 915

(51) Int. Cl.
*A61K 8/00*    (2006.01)
*C08C 45/00*   (2006.01)

(52) U.S. Cl. ............................ 512/25; 510/102; 512/8; 512/27; 568/341; 568/350; 568/375; 568/377

(58) Field of Classification Search ................. 510/102; 512/8, 27; 568/341, 350, 375, 377
See application file for complete search history.

(56) References Cited

U.S. PATENT DOCUMENTS 3,718,696 A  *  2/1973  Mookherjee et al. ........ 568/346
6,815,413 B2 * 11/2004  Eh et al. ....................... 512/27

FOREIGN PATENT DOCUMENTS

DE    21 11 753         10/1971
EP    1 201 738 A1       5/2002

* cited by examiner

*Primary Examiner*—Terressa M Boykin
(74) *Attorney, Agent, or Firm*—Roylance, Abrams, Berdo & Goodman, L.L.P.

(57) ABSTRACT

The invention relates to a method for producing cyclohexadecanone by hydrogenating cyclohexadecenone, to mixtures of aromatic substances, and to products containing the inventive cyclohexadecanone.

14 Claims, No Drawings

METHOD FOR PRODUCING CYCLOHEXADECANONE

The present invention relates to a process for the production of cyclohexadecanone by hydrogenation of cyclohexadecenone and odoriferous substance (fragrance) mixtures as well as products containing the cyclohexadecanone according to the invention.

Macrocyclic ketones with 14-membered to 18-membered rings are generally known as musk fragrances. Cyclohexadecanone is contained for example in glandular secretions of some types of civet cats (K. Bauer, A. Garbe, H. Surburg, Common Fragrance and Flavor Materials, p. 169, Wiley-VCH, Weinheim, 1997).

Cyclohexadecanone can be produced according to DE-A 2 111 753 by hydrogenation of 8-cyclohexadecenone. In the hydrogenation described there, very large amounts of hydrogenation catalysts are employed.

In EP-A 1 201 738 cyclohexadecanone is produced by hydrogenation of 8-cyclohexadecenone on palladium in ethanol. The weight ratio of palladium to cyclohexadecenone was 1:603, and the yield was about 76% of theory.

In Chemistry Letters, 1973, 667-670, cyclohexadecanone was produced from 5-cyclohexadecenone by means of hydrogenation. No reaction conditions are given.

There is therefore a need to find a process that yields cyclohexadecanone economically and in good perfumery quality, in particular on an industrial scale.

The present invention provides a process for the production of cyclohexadecanone by hydrogenation of cyclohexadecenone in the presence of metallic palladium, characterised in that the weight ratio of palladium to cyclohexadecenone is below 1:5000.

The present invention also provides solutions, odoriferous substance mixtures and products, preferably perfumed products, containing the cyclohexadecanone produced according to the invention.

For the process according to the invention the weight ratio of palladium to cyclohexadecenone is below 1:5000, advantageously in the range from 1:8000 to 1:5,000,000, preferably in the range 1:12,000 to 1:2,000,000, particularly preferably in the range 1:20,000 to 1:800,000 and most particularly preferably in the range from 1:25,000 to 1:500,000.

The amount of palladium refers in this connection to the absolute content of palladium, i.e. without carrier material and without the possible presence of water or diluents.

Cyclohexadecenones within the meaning of the invention may contain 1 to 3 olefinic double bonds, cyclohexadecenones with 1 olefinic double bond being preferred.

According to the invention (E)- or (Z)-cyclohexadecenone and arbitrary mixtures of these (E)- or (Z)-isomers may be used. According to the invention all regioisomeric cyclohexadecenones and arbitrary mixtures of these compounds may be used. It is preferred to use 5-cyclohexadecenone and 8-cyclohexadecenone, particularly preferred being 8-cyclohexadecenone, wherein an (E):(Z) ratio of 1:10 to 10:1 is preferred, a ratio of 1:5 to 5:1 is particularly preferred and a ratio of 1:3 to 4:1 is most particularly preferred. In a particularly advantageous modification 8-cyclohexadecenone is used with an (E):(Z) ratio of 1:1 to 3:1.

Cyclohexadecenones and processes for their production are described for example in J. Org. Chem. 1971, 36, 3266-3270; J. Org. Chem. 1971, 36, 4124-4125; Tetrahedron Lett. 1965, 21, 1537-1540 or also in Bull. Chem. Soc. Jpn. 1980, 53, 2958-2961.

The cyclohexadecenones used in the process according to the invention preferably have a good odoriferous quality, i.e. the cyclohexadecenones that are employed do not contain any chemically and odoriferously significant interfering impurities. The chemical purity is preferably >96 wt. %, particularly preferably >98 wt. %.

The palladium may for example be used in finely divided form, applied to carriers or together with other metals (e.g. mixtures, alloys). The catalysts may be doped with one or more arbitrary metals.

The palladium may be applied to organic or inorganic carrier materials. The catalysts may contain a carrier material or mixtures of carrier materials. As advantageous carrier materials there may be mentioned activated charcoal, charcoal, aluminium oxides, metal oxides, silica gels, zeolites, clays, granulated clays, amorphous aluminium silicates, or other inorganic carriers. A preferred carrier material is activated charcoal.

A particularly preferred catalyst is palladium on activated charcoal.

If catalysts containing carrier materials are employed, then the amount of palladium on the carrier material is generally 0.5 to 50 wt. %, preferably 1 to 20 wt. %, particularly preferably 3 to 10 wt. % and most particularly preferably 4 to 7 wt. %, referred to the dry catalyst.

For the process according to the invention the catalyst may be used in the dry or wet state (residual moisture consisting of water).

It is also possible to produce the palladium metal in situ before the start of or during the hydrogenation by reduction with hydrogen from corresponding compounds such as oxides or salts, in which the palladium may optionally be deposited on a carrier. Suitable for this purpose are for example palladium halides such as palladium(II) chloride.

The process according to the invention may be carried out using diluents or mixtures of diluents. Diluents that are inert under the employed hydrogenation conditions are suitable, such as for example monohydric or polyhydric alcohols, aqueous mixtures containing monohydric or polyhydric alcohols, ketones, ethers, esters, aromatic or saturated hydrocarbons. Preferred are alcohols with 1 to 4 carbon atoms, alkanes with 5 to 15 carbon atoms, ketones with 3 to 8 carbon atoms, open-chain or cyclic ethers with 4 to 10 carbon atoms, esters with 3 to 12 carbon atoms or aromatic hydrocarbons with 6 to 10 carbon atoms. There may typically be used diluents such as methanol, ethanol, isopropanol, n-propanol, isobutanol, n-butanol, sec.-butanol, tetrahydrofuran, dibutyl ether, ethylene glycol dimethyl ether, acetone, butanone, 2-pentanone, 3-pentanone, hexanone, cyclohexanone, methyl ethyl ketone, diethyl ketone, diisopropyl ketone, methyl isobutyl ketone, ethyl acetate, methyl acetate, n-pentane, n-hexane, n-heptane, n-octane, isooctane, cyclopentane, cyclohexane, methylcyclohexane, cyclooctane, benzene, toluene, ethylbenzene, xylenes; preferred are ethanol, isopropanol, acetone, methyl ethyl ketone and toluene.

Also preferred are diluents that are acceptable as regards perfumery, dermatological or cosmetic criteria. Such diluents are preferably ethanol, dipropyiene glycol, propylene glycol, 1,2-butylene glycol, glycerol, diethylene glycol monoethyl ether, diethyl phthalate, isopropyl myristate, triethyl citrate; benzyl benzoate and benzyl acetate. Particularly preferred are ethanol, diethyl phthalate, propylene glycol, dipropylene glycol, triethyl citrate and isopropyl myristate.

The weight ratio of cyclohexadecenone and diluent is advantageously in the range from 1:10 to 4:1, preferably, in the range from 1:5 to 3:1, particularly preferably in the range from 1:2 to 2:1. In a preferred embodiment the proportion of cyclohexadecenone is 40 to 80 wt. %, particularly preferably 45 to 75 wt. %, referred to the mixture of cyclohexadecenone and diluent.

The hydrogenation may be carried out in the presence of diluents at temperatures of 0° to 150° C. Advantageously temperatures in the range from 10° to 100° C., preferably in the range from 20° to 85° C. and particularly preferably in the range from 30° to 60° C. are employed.

The hydrogenation may also be carried out in the absence of diluents at temperatures above 60° C., preferably in the range from 70° to 150° C., particularly preferably at 70° to 100° C. A high and/or excessively long thermal stress has a deleterious effect on the odoriferous quality of the cyclohexadecanone. After the hydrogenation in the absence of diluents a purification step is preferably carried out, which preferably comprises a recrystallisation.

According to the invention the hydrogenations are carried out with elementary hydrogen.

The hydrogen pressure is suitably 1 to 100 bar, preferably 1 to 30 bar, particularly preferably 3 to 20 bar and most particularly preferably 5 to 15 bar.

The reaction time of the hydrogenation is preferably 2 to 80 hours, particularly preferably 5 to 40 hours and most particularly preferably 8 to 25 hours.

Following the hydrogenation it may be advantageous, particularly as regards the odoriferous quality, to carry out a recrystallisation after separating the catalyst.

The recrystallisation is particularly advantageously carried out using alcohols with 1 to 8 carbon atoms, alkanes with 5 to 15 carbon atoms, ketones with 3 to 8 carbon atoms, open-chain or cyclic ethers with 4 to 10 carbon atoms, esters with 3 to 12 carbon atoms or aromatic hydrocarbons with 6 to 10 carbon atoms. Preferred are methanol, ethanol, isopropanol, n-propanol, isobutanol, n-butanol, sec.-butanol, tetrahydrofuran, dibutyl ether, ethylene glycol dimethyl ether, acetone, butanone, 2-pentanone, 3-pentanone, hexanone, cyclohexanone, methyl isobutyl ketone, ethyl acetate, methyl acetate, n-pentane, n-hexane, n-heptane, n-octane, isooctane, cyclopentane, cyclohexane, methylcyclohexane, cyclooctane, benzene, toluene, ethylbenzene, xylenes; particularly preferred are methanol, ethanol, acetone, isopropanol, and toluene.

In a particularly advantageous embodiment the thermal treatment during the overall process, i.e. the hydrogenation and the optionally subsequent purification (e.g. crystallisation or distillation) is carried out at temperatures of less than or equal to 150° C., preferably at temperatures less than or equal to 130° C. and particularly preferably at temperatures less than or equal to 100° C.

The cyclohexadecanone produced according to the invention is a very complex musk compound and has a valuable odoriferous spectrum. In perfumery terms cyclohexadecanone manifests marked similarities to muscone and cyclopentadecanone as well as a strong macromusk note, and in addition to this cyclohexadecanone is characterised by the pronounced "animal" note of musk tincture or natural tonkin musk. Further odoriferously interesting aspects are ambrette and nitromusk, with a certain accompanying fruitiness.

The cyclohexadecanone produced according to the invention already possesses as hydrogenation crude product, especially if the hydrogenation is carried out in the presence of diluents, a good perfumery quality. Hydrogenation crude product is understood to denote the product derived directly from the hydrogenation, after removal of the hydrogenation catalyst. The hydrogenation crude product may for example be present as immediate solution in the diluent used in the hydrogenation, enriched in this by partial removal of the diluent, or obtained as pure substance after removal of the diluent.

If the hydrogenation crude product is to be used as solution or is to be processed further, then it is advantageous to carry out the hydrogenation in the presence of a diluent that is acceptable for perfumery, dermatological or cosmetic use, so that the solution containing the hydrogenation crude product can be employed as such. The hydrogenation crude product according to the invention may be used, in particular as a solution in the diluent in the presence of which the hydrogenation was carried out, without further purification steps as an odoriferous substance, in perfumery compositions and for imparting a pleasant smell.

The process according to the invention may for example be carried out as follows:

Cyclohexadecenone and the catalyst and optionally a diluent are placed in a pressurised vessel equipped with a stirrer. Hydrogenation is carried out at the chosen reaction temperature and hydrogen pressure. The hydrogenation crude product is typically obtained after removal of the catalyst by filtration, decanting or centrifugation. In the case of a diluent-free hydrogenation the separation of the catalyst must be carried out at elevated temperature, which advantageously is above the melting point of the cyclohexadecanone. A more comprehensive purification may optionally be carried out, for example by distillation, crystallisation or steam treatment. The cyclohexadecanone can be obtained in an almost quantitative yield (generally greater than 97 wt. %) by the process according to the invention.

Cyclohexadecanone can be produced in a high state of purity and in very good yield by the process according to the invention. The process according to the invention is therefore particularly advantageous from economic, technical and industrial aspects.

The cyclohexadecanone produced by the process according to the invention may in particular be used as an odoriferous substance, in perfumery compositions, perfumery oils, odoriferous substance mixtures or aroma compositions.

Odoriferous substances with which cyclohexadecanone may be combined are described for example in Bauer, Garbe, Surburg, Common Fragrance and Flavor Materials, Wiley-VCH, $4^{th}$ Edition, 2001.

A further area of application of cyclohexadecanone or of odoriferous substance mixtures containing cyclohexadecanone are perfumed products, preferably hygiene or body care products, especially in the household and body care sector.

Cyclohexadecanone is characterised in particular by a good adsorption on synthetic and natural fibres, hair, as well as the skin.

The perfumery oils containing the cyclohexadecanone produced according to the invention may be used in concentrated form, in solutions or in another modified form for the production of, for example, perfume extracts, eau de parfums, eau de toilettes, aftershave lotions, eau de colognes, pre-shave products, splash colognes and perfumed freshener wipes as well as the perfuming of acidic, alkaline and neutral cleaning agents such as e.g. floor-cleaning agents, window-cleaning agents, washing-up liquids and dishwasher formulations, bath and sanitaryware cleaning agents., scouring agents, solid and liquid WC-cleaning agents, powder-type and foam-type carpet-cleaners, liquid detergents, pulverulent detergents, wash pre-treatment agents such as bleaching agents, soaking agents and stain-removers, textile softeners, washing soaps, washing tablets, disinfectants, surface disinfectants as well as air-fresheners in liquid or gel-like form or applied to a solid carrier, aerosol sprays, waxes and polishes such as furniture polishes, floor waxes, shoe creams as well as body care agents, such as for example solid and liquid soaps, shower gels, shampoos, shaving soaps, shaving foams, bath oils, cosmetic emulsions of the oil-in-water, water-in-oil and water-in-oil-in-water type, such as e.g. skin creams and lotions, face creams and lotions, sunscreens and lotions, aftersun creams and lotions, hand creams and lotions, foot creams and lotions, depilation creams and lotions, aftershave creams and lotions, tanning creams and lotions, hair care products such as e.g. hairsprays, hair gels, hair lotions, hair rinses, permanent and semi-permanent hair dyes, hair-shaping means such as cold waves and hair smoothing agents, hair tonics, hair creams and lotions, deodorants and antiperspirants such as e.g. underarm sprays, roll-ons, deodorant sticks, deodorant creams or decorative cosmetics products.

The following examples illustrate the invention.

EXAMPLE 1

In Example 1 the ratio of Pd:8-cyclohexadecenone is about 1:18,520.

100 kg of 8-cyclohexadecenone (odoriferously good quality; the gas chromatography (GC) ratio of (E) and (Z) isomers was 3:1) and 180 g of palladium on activated charcoal (Pd content: 5 wt. %) with 40% water content were placed in a stirred autoclave equipped with a gassing stirrer. The reaction mixture was hydrogenated for 17 hours at 75° C. and 20 bar hydrogen pressure and then filtered at about 75° C. The yield of hydrogenation crude product was >98% (GC content of cyclohexadecanone: >97%). The perfumery quality could be improved still further by recrystallisation from methanol or by steam treatment.

EXAMPLE 2

In Example 2 the ratio of Pd:8-cyclohexadecenone is about 1:7,500.

180 kg of 8-cyclohexadecenone (odoriferously good quality: GC ratio of (E) and (Z) isomers: 65:34) in 180 kg of diethyl phthalate and 800 g of palladium on activated charcoal (Pd content: 5 wt. %) with 40% water content were placed in a stirred autoclave equipped with a gassing stirrer. The reaction mixture was hydrogenated for 20 hours at 49° to 52° C. and 5 bar hydrogen pressure. After filtration 349 kg of cyclohexadecanone were obtained as 50% solution in diethyl phthalate. The yield of cyclohexadecanone in terms of conversion was >99%. The product thereby obtained was of a good perfumery quality.

EXAMPLE 3

In Example 3 the ratio of Pd:8-cyclohexadecenone is about 1:15,000.

180 kg of 8-cyclohexadecenone (odoriferously good quality: GC ratio of (E) and (Z) isomers: 64:34.5) in 180 kg of isopropyl myristate and 400 g of palladium on activated charcoal (Pd content: 5 wt. %) with 40% water content were placed in a stirred autoclave equipped with a gassing stirrer. The reaction mixture was hydrogenated for 40 hours at 4 to 5 bar hydrogen pressure, in which connection the temperature was raised during the course of the hydrogenation from the initial value of 50° C. to 125° C. After filtration 346 kg of cyclohexadecanone were obtained as 50% solution in isopropyl myristate. The yield of cyclohexadecanone in terms of conversion was >99%. The product thereby obtained was of a good perfumery quality.

EXAMPLE 4

In Example 4 the ratio of Pd:8-cyclohexadecenone is about 1:33,333.

100 kg of 8-cyclohexadecenone (odoriferously good quality: GC ratio of (E) and (Z) isomers was 2.5:1), 45 kg of acetone and 100 g of palladium on activated charcoal (Pd content: 5 wt. %) with 40% water content were placed in a stirred autoclave equipped with a gassing stirrer. The reaction mixture was hydrogenated for 12 hours at 35° to 40° C. and at 15 bar hydrogen pressure and then filtered. After removing the acetone 99.2 kg of cyclohexadecanone were obtained (GC content of cyclohexadecanone: >98%). The product thereby obtained was of a good perfumery quality. The perfumery quality could be improved still further by recrystallisation from methanol.

EXAMPLE 5

In Example 5 the ratio of Pd:8-cyclohexadecenone is about 1:5,556.

1000 kg of 8-cyclohexadecenone (odoriferously good quality: GC ratio of (E) and (Z) isomers was 2:1) in 1000 kg of ethanol and 6 kg of palladium on activated charcoal (Pd content: 5 wt. %) with 40% water content were placed in a stirred autoclave equipped with a gassing stirrer. The reaction mixture was hydrogenated for 18 hours at 30° to 50° C. and 6 bar hydrogen pressure. After filtration 2002 kg of a 50% solution of cyclohexadecanone in ethanol (GC purity without ethanol >97%) were obtained. The yield of cyclohexadecanone was >99%. The product thereby obtained was of a good perfumery quality. The perfumery quality could be improved still further by recrystallisation from ethanol.

EXAMPLE 6

In Example 6 the ratio of Pd:8-cyclohexadecenone is about 1:7,778.

700 g of 8-cyclohexadecenone (odoriferously good quality: GC ratio of (E) and (Z) isomers was 63.4:35.5), 300 g of acetone and 3 g of palladium on activated charcoal (Pd content: 5 wt. %) with 40% water content were placed in a stirred autoclave equipped with a gassing stirrer. The reaction mixture was hydrogenated for 8 hours at 55° to 60° C. and 5 bar hydrogen pressure. 992 g of hydrogenation crude product were obtained, and the GC purity of the cyclohexadecanone was 99.4% (the acetone was disregarded). The product thereby obtained was of a good perfumery quality.

EXAMPLE 7

In Example 7 the ratio of Pd:8-cyclohexadecenone is about 1:6,667.

800 g of 8-cyclohexadecenone (odoriferously good quality: ratio of (E) and (Z) isomers was 1.8:1), 400 g of acetone and 4 g of palladium on activated charcoal (Pd content: 5 wt. %) with 40% hydrogen content were placed in a stirred autoclave equipped with a gassing stirrer. The reaction mixture was hydrogenated for 8 hours at 25° C. and 18 bar hydrogen pressure and then filtered. 991 g of hydrogenation crude product were obtained, the GC purity of the cyclohexadecanone being 99.3% (the acetone was disregarded). The product thereby obtained was of a good perfumery quality.

EXAMPLE 8

In Example 8 the ratio of Pd:8-cyclohexadecenone is about 1:8,317.

998 g of 8-cyclohexadecenone (odoriferously good quality: GC ratio of (E) and (Z) isomers was 63.4:35.5) and 4 g of palladium on activated charcoal (Pd content: 5 wt. %) with 40% water content Were placed in a stirred autoclave equipped with a gassing stirrer. The reaction mixture was hydrogenated for 15 hours at 95° C. and 18 bar hydrogen pressure and then filtered at about 95° C. The yield of hydrogenation crude product was >98% (GC content of cyclohexadecanone was 96%). The perfumery quality could be improved still further by recrystallisation from methanol or by steam treatment.

The invention claimed is:

1. Process for the production of cyclohexadecanone by hydrogenation of cyclohexadecenone in the presence of a hydrogenation catalyst comprising metallic palladium in a weight ratio of palladium to cyclohexadecenone, characterized in that the weight ratio of palladium to cyclohexadecenone is below 1:5,000.

2. Process according to claim 1, characterized in that the weight ratio of cyclohexadecenone is in the range from 1:8,000 to 1:5,000,000.

3. Process according to claim 1, characterized in that palladium on activated charcoal is used as said hydrogenation catalyst.

4. Process according to claim 1, characterized in that the cyclohexadecenone is 8-cyclohexadecenone.

5. Process according to claim 1, characterized in that the hydrogenation is carried out in the presence of a diluent, and the weight ratio of cyclohexadecenone and diluent is in the range from 1:10 to 4:1.

6. Process according to claim 1, characterized in that the hydrogenation is carried out in the absence of a diluent at temperatures in the range from 70.degree. to 150.degree. C.

7. Process according to claim 1, characterized in that the hydrogenation is carried out in a diluent that is acceptable as regards perfumery, dermatological or cosmetic criteria.

8. Process according to claim 1, characterized in that the diluent comprises ethanol, isopropanol, acetone, methyl ethyl ketone, toluene, diethyl phthalate, propylene glycol, dipropylene glycol, triethyl citrate and or isopropyl myristate.

9. Process according to claim 1, characterized in that after the hydrogenation a recrystallization is carried out.

10. Process according to claim 1, characterised characterized in that the reaction time of the hydrogenation is 2 to 80 hours.

11. Solutions containing the cyclohexadecanone produced according to the process of claim 1.

12. Solutions according to claim 11, wherein said hydrogenation is performed with a diluent that is acceptable as regards perfumery, dermatological or cosmetic criteria.

13. Odoriferous substance mixtures containing the cyclohexadecanone produced according to claim 1.

14. Product containing the cyclohexadecanone produced according to claim 1.

* * * * *

UNITED STATES PATENT AND TRADEMARK OFFICE
CERTIFICATE OF CORRECTION

PATENT NO.        : 7,674,765 B2                                           Page 1 of 1
APPLICATION NO.   : 10/516006
DATED             : March 9, 2010
INVENTOR(S)       : Ingo Wohrle et al.

It is certified that error appears in the above-identified patent and that said Letters Patent is hereby corrected as shown below:

Column 2, line 58, change "dipropyiene" to "dipropylene"; and
    Claim 10 (column 8, line 17), delete "characterised".

Signed and Sealed this

Eleventh Day of May, 2010

David J. Kappos
*Director of the United States Patent and Trademark Office*